United States Patent [19]

Moon et al.

[11] Patent Number: 5,648,234
[45] Date of Patent: Jul. 15, 1997

[54] EXPRESSION VECTOR FOR PHYTOLACCA ANTIVIRAL PROTEIN

[75] Inventors: Young-Ho Moon, Kyunggi-do; Hong-Seob Jeon, Seoul; Kyu-Whan Choi, Seoul; Kwan-Ho Lee, Seoul; Man-Keun Kim, Seoul, all of Rep. of Korea

[73] Assignee: Jinro Limited, Seoul, Rep. of Korea

[21] Appl. No.: 342,786

[22] Filed: Nov. 21, 1994

Related U.S. Application Data

[63] Continuation of Ser. No. 147,024, Nov. 1, 1993, abandoned.

[30] Foreign Application Priority Data

Jul. 2, 1993 [KR] Rep. of Korea ............................. 93-12

[51] Int. Cl.$^6$ ........................... C12N 15/29; C12N 1/20; C12N 15/63
[52] U.S. Cl. ................. 435/69.1; 435/252.8; 435/320.1; 536/23.6
[58] Field of Search ................................. 435/69.1, 200, 435/252.33, 320.1; 530/379

[56] References Cited

U.S. PATENT DOCUMENTS

| | | | |
|---|---|---|---|
| 4,363,758 | 12/1982 | Masuhu et al. | 530/370 |
| 5,101,025 | 3/1992 | Piatak, Jr. et al. | 435/320.1 |
| 5,348,865 | 9/1994 | Moon et al. | 435/320.1 |
| 5,416,202 | 5/1995 | Bernhard et al. | 435/320.1 |
| 5,484,889 | 1/1996 | Lee-Hwang et al. | 530/379 |

OTHER PUBLICATIONS

*Isolation and Analysis of a Genomic Clone Encoding a Pokeweed Antiviral Protein*, (Kataoka, J.) Plant Mol.Biol., 20:879–886 (1992).

J.D. Irvin —Purification and Partial Characterization of the Antiviral Protein from Phytolacca americana which Inhibits Eukaryotic Protein from Phytolacca americana which Inhibits Eukaryotic Protein Synthesis; Arch. Biochem. Biophys., 169, 522–528 (1975).

K.C. Halling et al. —Genomic Cloning and Characterization of a Ricin Gene from Ricinus communis; Nucleic Acid Res., 13, 8019–8033 (1985).

J. Kataoka et al. —DNA Sequence of Mirabilis Antiviral Protein (MAP), a Ribosome–inactivating Protein with an Antiviral Property, from Mirabilis jalapa L. and Its Expression in Escherichia coli; J.Biol. Chem., 266, 8426–8430 (1991).

X. Zhang et al. —Homology of Trichosanthin and Ricin A Chain; Nature, 321, 477–478 (1986).

Y.Endo et al. —The RNA N–Glycosidase Activity of Ricin A–Chain; J. Biol. Chem., 263, 8735–8739 (1988).

J.D. Irvin et al. —Purification and Properties of a Second Antiviral Protein from Phytolacca americana Which inactivates Eukaryotic Ribosomes; Arch. Biochem. Biophys., 200, 418–425 (1980).

B. Jansen et al. —Establishment of a Human t(4;11) Leukemia in Severe Combined Immunodeficient Mice and successful Treatment Using Anti–CD19 (B43)–Pokeweed Antiviral Protein Immunotoxin; Cancer Res., 52, 406–412 (1992).

Y.W. Kim et al. —Immunoconjugates That Neutralize HIV Virions Kill T cells Infected with Diverse Strains of HIV–1; J. Immunol., 144, 1257–1262 (1990).

D.E. Myers et al. —Production of a Pokeweed Antiviral Protein(PAP)–containing Immunotoxin, B43–PAP, Directed Against the CD19 Human B Lineage Lymphoid Differentiation Antigen in Highly Purified Form for Human Clinical Trails; J. Immunol. Methods, 136, 221–238 (1991).

M.P. Ready et al. —Extracellular Location of Pokeweed Antiviral Protein; Proc. Natl. Acad. Sci. USA, 83, 5053–5056 (1986).

Q. Lin et al. —Isolation and characterization of a cDNA Clone Encoding the Anti–viral Protein from Phytolacca americana; Plant Mol. Biol., 17, 609–614 (1991).

Kataoka et al, "Expression of a pokeweed antiviral protein in E. coli . . . " *FEBS Lett.* 320(1):31–34 (Mar. 1993).

Gheran et al, *ATCC Catalog*, 1992, p. 137.

Lodge et al, "Characterization and Cloning of the Pokeweed Antiviral Protein", *J. Cell. Biochem.*, Suppl. 14E:304 (1990).

*Primary Examiner*—Vasu Jagannthon
*Assistant Examiner*—Christine Saoud
*Attorney, Agent, or Firm*—Darby & Darby

[57] ABSTRACT

The present invention provides a novel expression vector for Phytolacca antiviral protein isolated from *Phytolacca americana* L. and a microorganism transformed with said PAP expression vector. In accordance with the present invention, biologically active PAP can be produced in a massive manner from the microorganism transformed with the expression vector of the invention; and, therefore, the recombinant PAP can be practically applied to various fields, e.g., the molecular studies on PAP and treatment of AIDS employing immunoconjugate.

3 Claims, 7 Drawing Sheets

FIG. 1A

```
  1  GAGGAGAGAG AACTAGTTAG TAGGAAGGGA AGATGAAGTC GATGCTTGTG GTGACAATAT
 61  CAATATGGCT CATTCTTGCA CCAACTTCAA CTTGGGCTGT GAATACAATC ATCTACAATG
121  TTGGAAGTAC CACCATTAGC AAATACGCCA CTTTTTCTGAA TGATCTTCGT AATGAAGCGA
181  AAGATCCAAG TTTAAAATGC TATGGAATAC CAATGCTGCC CAATACAAAT ACAAATCCAA
241  AGTACGTGTT GGTTGAGCTC CAAGGTTCAA ATAAAAAAAC CATCACACTA ATGCTGAGAC
301  GAAACAATTT GTATGTGATG GGTTATTCTG ATCCCTTTGA AACCACTAAA TGTCGTTACC
361  ATATCTTTAA TGATATCTCA GGTACTGAAC GCCAAGATGT AGAGACTACT CTTTGCCCAA
421  ATGCCAATTC TCGTGTGAGT AAAAACATAA ACTTTGATAG TCGATATCCA ACATTGGAAT
481  CAAAAGCGGG AGTAAAATCA AGAAGTCAAG TCCAACTGGG AATTCAAATA CTCGACAGTA
541  ATATTGGAAA GATTTCTGGA GTGATGTCAT TCACTGAGAA AACCGAAGCC GAATTCCTAT
601  TGGTAGCCAT ACAAATGGTA TCAGAGGCAG CAAGATTCAA GTACATAGAG AATCAGGTGA
```

FIG. IB

```
 661  AAACTAATTT TAACAGAGCA TTCAACCCTA ATCCCAAAGT ACTTAATTTG CAAGAGACAT
 721  GGGTAAGAT  TTCAACAGCA  ATTCATGATG  CCAAGAATGG  AGTTTTACCC  AAACCTCTCG
 781  AGCTAGTGGA TGCCAGTGGT GCCAAGTGGA TAGTGTTGAG AGTGGATGAA ATCAAGCCTG
 841  ATGTAGCACT CTTAAACTAC GTTGGTGGGA GCTGTCAGAC AACTTATAAC CAAAATGCCA
 901  TGTTCCCTCA ACTTATAATG ATAATTACAT GGTTAATCTT GGTGATCTAT
 961  TTGAAGGATT CTGATCATAA ACTTAATAAG GAGTATATAT ATATTACTCC AACTATATTA
1021  TAAAGCTTAA ATAAGAGGCC GTGTTAATTA GTACTTGTTG CCTTTTGCTT TATGGTGTTG
1081  TTTATTATGC CTTGTATGCT TGTAATATTA TCTAGAGAAC AAGATGTACT GTGTAATAGT
1141  CTTGTTTGAA ATAAACTTC  CAATTATGAT GCAAAAAAAA AAAAAAAAA  AAAAA
```

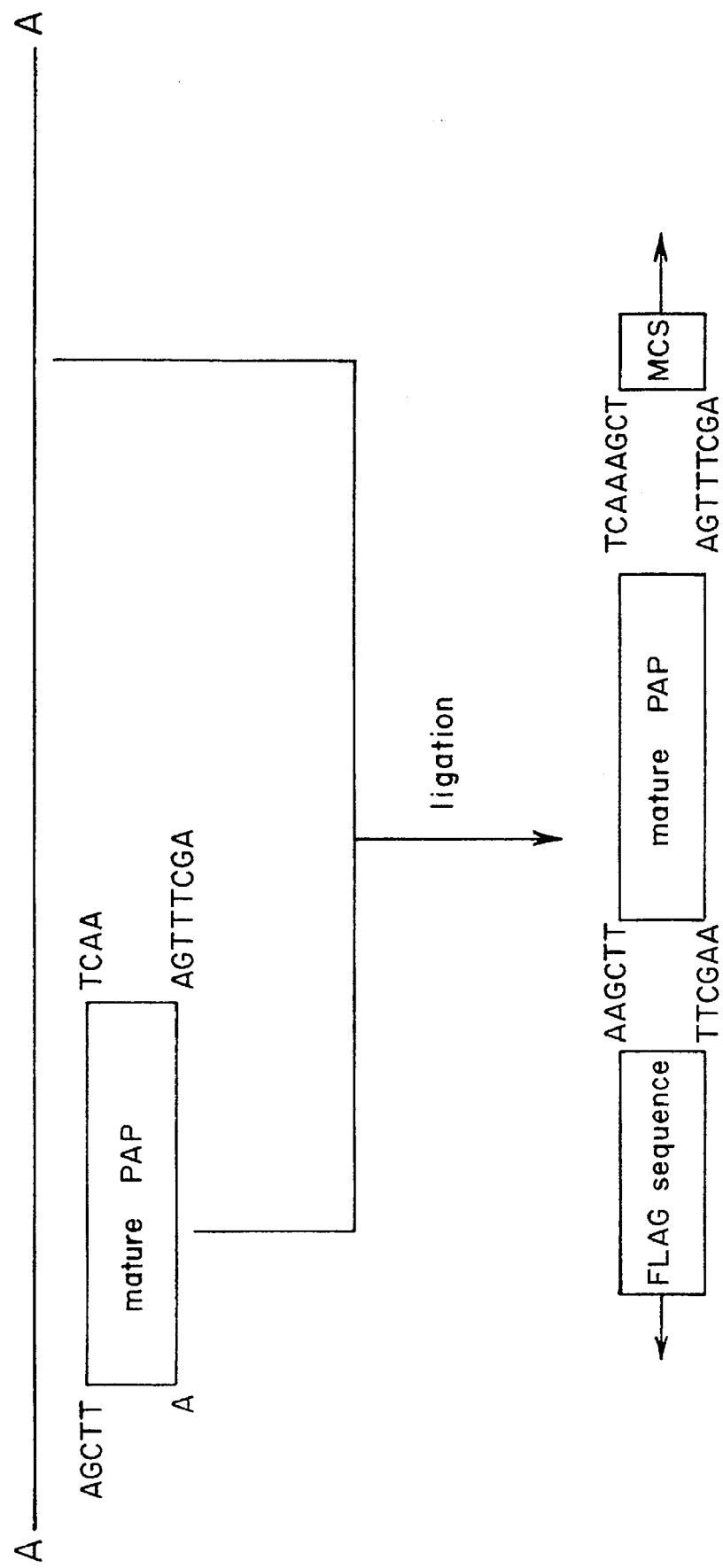

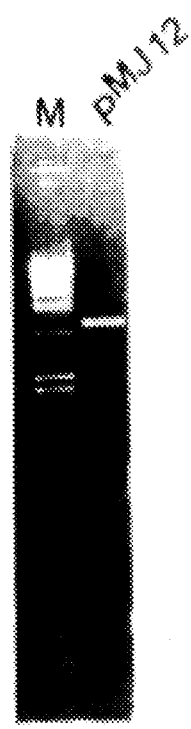
FIG. 3
FIG. 5
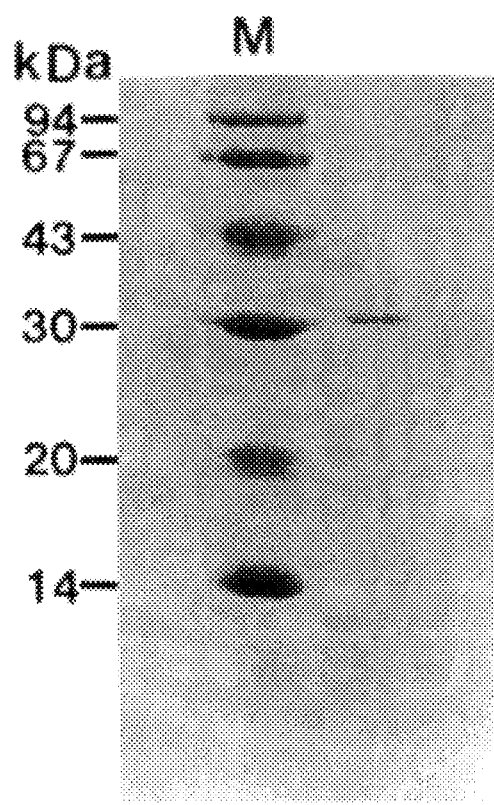

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1195 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: NO ( v i ) ORIGINAL SOURCE:
        ( A ) ORGANISM: Phytolacca americana L.

( v i i ) IMMEDIATE SOURCE:
        ( B ) CLONE: PAP ( x i ) SEQUENCE DESCRIPTION: SEQ ID NO:1:

```
GAGGAGAGAG    AACTAGTTAG    TAGGAAGGGA    AGATGAAGTC    GATGCTTGTG    GTGACAATAT         60

CAATATGGCT    CATTCTTGCA    CCAACTTCAA    CTTGGGCTGT    GAATACAATC    ATCTACAATG        120

TTGGAAGTAC    CACCATTAGC    AAATACGCCA    CTTTTCTGAA    TGATCTTCGT    AATGAAGCGA        180

AAGATCCAAG    TTTAAAATGC    TATGGAATAC    CAATGCTGCC    CAATACAAAT    ACAAATCCAA        240

AGTACGTGTT    GGTTGAGCTC    CAAGGTTCAA    ATAAAAAAAC    CATCACACTA    ATGCTGAGAC        300

GAAACAATTT    GTATGTGATG    GGTTATTCTG    ATCCCTTTGA    AACCAATAAA    TGTCGTTACC        360

ATATCTTTAA    TGATATCTCA    GGTACTGAAC    GCCAAGATGT    AGAGACTACT    CTTTGCCCAA        420

ATGCCAATTC    TCGTGTTAGT    AAAAACATAA    ACTTTGATAG    TCGATATCCA    ACATTGGAAT        480

CAAAAGCGGG    AGTAAAATCA    AGAAGTCAAG    TCCAACTGGG    AATTCAAATA    CTCGACAGTA        540

ATATTGGAAA    GATTTCTGGA    GTGATGTCAT    TCACTGAGAA    AACCGAAGCC    GAATTCCTAT        600

TGGTAGCCAT    ACAAATGGTA    TCAGAGGCAG    CAAGATTCAA    GTACATAGAG    AATCAGGTGA        660

AAACTAATTT    TAACAGAGCA    TTCAACCCTA    ATCCCAAAGT    ACTTAATTTG    CAAGAGACAT        720
```

| | | | | | |
|---|---|---|---|---|---|
|GGGGTAAGAT|TTCAACAGCA|ATTCATGATG|CCAAGAATGG|AGTTTTACCC|AAACCTCTCG 780|
|AGCTAGTGGA|TGCCAGTGGT|GCCAAGTGGA|TAGTGTTGAG|AGTGGATGAA|ATCAAGCCTG 840|
|ATGTAGCACT|CTTAAACTAC|GTTGGTGGGA|GCTGTCAGAC|AACTTATAAC|CAAAATGCCA 900|
|TGTTTCCTCA|ACTTATAATG|TCTACTTATT|ATAATTACAT|GGTTAATCTT|GGTGATCTAT 960|
|TTGAAGGATT|CTGATCATAA|ACTAATAAG|GAGTATATAT|ATATTACTCC|AACTATATTA 1020|
|TAAAGCTTAA|ATAAGAGGCC|GTGTTAATTA|GTACTTGTTG|CCTTTTGCTT|TATGGTGTTG 1080|
|TTTATTATGC|CTTGTATGCT|TGTAATATTA|TCTAGAGAAC|AAGATGTACT|GTGTAATAGT 1140|
|CTTGTTTGAA|ATAAACTTC|CAATTATGAT|GCAAAAAAAA|AAAAAAAAA|AAAAA 1195|

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Phytolacca americana L.

( v i i ) IMMEDIATE SOURCE:
        ( B ) CLONE: PAP 5'primer ( x i ) SEQUENCE DESCRIPTION: SEQ ID NO:2:

CCAAGCTTGT  GAATACAATC  AAC                      23

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Phytolacca americana L.

( v i i ) IMMEDIATE SOURCE:
        ( B ) CLONE: PAP 3'primer ( x i ) SEQUENCE DESCRIPTION: SEQ ID NO:3:

GGAAGCTTTG  ATCAGAATCC  TTCAAA                 26

( 2 ) INFORMATION FOR SEQ ID NO:4:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Phytolacca americana L.

( v i i ) IMMEDIATE SOURCE:
        ( B ) CLONE: mature PAP 3'A ( x i ) SEQUENCE DESCRIPTION: SEQ ID NO:4:

TCAAAGCTTC  C                                    11

-continued ( 2 ) INFORMATION FOR SEQ ID NO:5:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Phytolacca americana L.

( v i i ) IMMEDIATE SOURCE:
( B ) CLONE: mature PAP 3'B ( x i ) SEQUENCE DESCRIPTION: SEQ ID NO:5:

AGTTTCGAAG G 11

EXPRESSION VECTOR FOR PHYTOLACCA ANTIVIRAL PROTEIN

This is a continuation of application Ser. No. 08/147,024, filed Nov. 1, 1993, now abandoned.

FIELD OF THE INVENTION

The present invention relates to a novel expression vector for an antiviral protein, more specifically, a recombinant expression vector for Phytolacca antiviral protein isolated from *Phytolacca americana* L. and a microorganism transformed therewith.

BACKGROUND OF THE INVENTION

Studies on the antiviral proteins from many different plant species have been carried out, starting from the discovery of pokeweed antiviral protein (or Phytolacca antiviral protein, hereinafter referred to as "PAP") isolated from a crude extract of *Phytolacca americana* L. (see: Irvin, J. D., *Arch. Biochemistry Biophys.*, 169:522–528 (1975)). In addition to PAP, a few antiviral proteins have been isolated from several plants, e.g., Ricin (from *Ricinus communis*) (see: Halting, K. C. et al., *Nucleic Acid Res.*, 13:8019–8033 (1985)), Mirabilia antiviral protein ("MAP", from *Mirabilia jalapa* L.) (see: Kataoka, J. et al., *J. Biol. Chem.*, 266:8426–8430 (1991)) and α-trichosanthin (from *Trichosanthes kirilowii*) (see: Zhang, X. et al., *Nature*, 321:477–478 (1986)). Said antiviral proteins have been reported to be ribosome inactivating proteins ("RIPs") having RNA N-glyoosidase activities (see: Endo, Y. et al., *J. Biol. Chem.*, 263:8735–8739 (1988)).

In general, PAP from *Phytolacca americana* U is classified as PAP-I, PAP-II and PAP-S that appear in spring leaves, summer leaves, and seeds, respectively; and it is reported that antiserum reactions of these PAPs are different from one another (see: Irvin, J. D. et al., *Arch. Biochemistry Biophys.*, 200:418–425 (1980)). Further, it has been known that ribosomes of *Phytolacca americana* L. are depurinated by the RNA N-glycosidase activity of PAP. On the other hand, an immunoconjugate of PAP with CD4 or CD19 has been reported to inhibit the replication of human immunodeficiency virus type I (see: Jansen, B. et al., *Cancer Res.*, 52:406–412 (1992); Kim Y. W. et al., *J. Immunol.*, 144:1257–1262 (1990)); Myers, D. E. et al., *J. Immunol. Methods*, 136:221–238 (1991)); in this connection, said PAPs have been proposed to be applicable to the treatment of AIDS. Accordingly, molecular biological studies on the PAPs have been actively carried out, including the nucleotide sequence analysis of cDNA of PAP; the elucidation of the precise mechanism of PAP's biological activity; construction of a transgenic plant; and, application to the immunoconjugate preparation.

The present inventors first developed a transgenic plant expressing PAP, and patent applications covering said expression vector are pending under the title "Expression vector for Phytolacca antiviral protein and process for preparing transgenic plant transformed thereof" (U.S. Ser. No. 08/049,075; EP appln. No. 93 110 445.9; JP appln. No. 5-128222). However, it is clear that the expression vector of the prior art is simply designed for the purpose of transformation of plants to confer viral resistance, in light of employing the CaMV 35S promoter which is generally used for the expression of plant genes.

Accordingly, the expression of PAP gene has been restricted to plants; and, therefore, there is a need in the art for the development of a practical expression vector which produces PAP at high levels in a versatile microorganism.

SUMMARY OF THE INVENTION

In accordance with the present invention, the present inventors, for the first time, developed a recombinant vector which expresses the PAP gene in a microorganism transformed therewith.

A primary object of the present invention is, therefore, to provide a novel recombinant expression vector containing the PAP gene isolated from a cDNA library of the *Phytolacca americana* L., which can be expressed in microorganisms with high yield.

Another object of the present invention is to provide a microorganism transformed therewith which expresses PAP in large quantities.

BRIEF DESCRIPTION OF DRAWINGS

The above and the other objects and features of the present invention will become apparent from following descriptions given in conjunction with the accompanying drawings, in which:

FIG. 1 is the full nucleotide sequence of the PAP gene isolated from a cDNA library of Phytolacca americana L. SEQ. ID. NO. 1;

FIG. 3 is a photograph showing the electrophoresis pattern of expression vector pMJ 12;

FIG. 5 is a photograph showing the SDS-PAGE pattern of PAP purified from *E. coli* HB101 harboring pMJ12;

DETAILED DESCRIPTION OF THE INVENTION

Figure 2A:
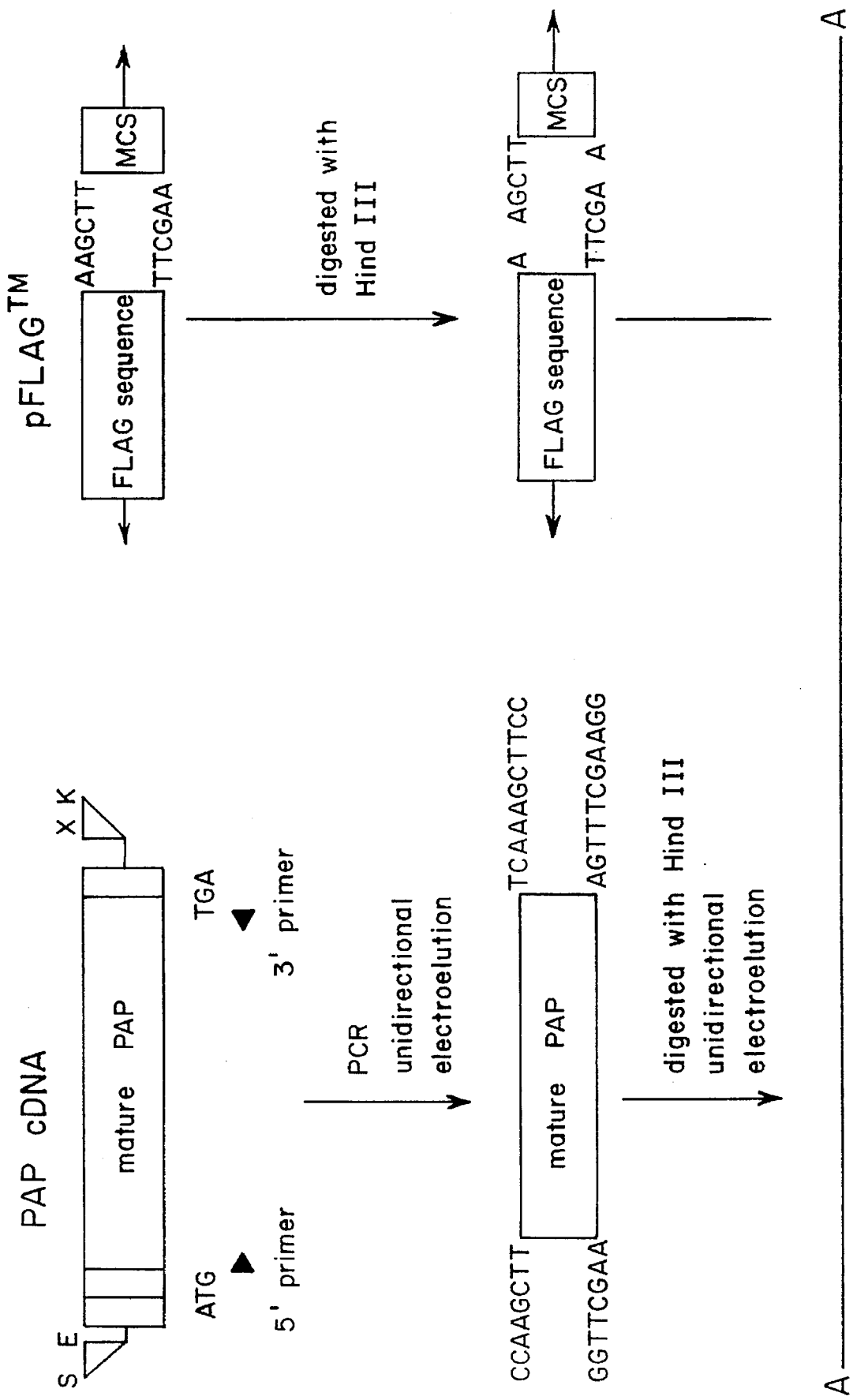
FIG. 2 is a scheme depicting a stepwise construction strategy for expression vector pMJ 12 of the invention wherein TCAAAGCTTCC SEQ ID NO:4 and AGTTTC-GAAGG SEQ ID NO:5 represent the 3' terminal sequence of the amplified mature PAP cDNA.

The present inventors developed a recombinant expression vector pMJ12, containing a PAP gene isolated from a cDNA library of *Phytolacca americana* L., which directs the expression of recombinant PAP in microorganisms transformed therewith.

To isolate the PAP gene, the inventors purified total cellular mRNA from leaves of *Phytolacca americana* L. obtained in Korea and constructed a cDNA library thereof. The PAP gene is selected by an immunoscreening method employing anti-PAP antibody; and, a deletion mutant is prepared from the isolated PAP gene using the Erase-a-Base system (Promega, U.S.A.). The DNA sequence of a cDNA clone containing the PAP gene (See. ID.NO.1 ) is determined by Sanger's dideoxy chain termination method (see: Sanger, F., *Science*, 214:1205–1210 (1981)).

For expression of the isolated PAP gene in microorganisms, a commercially available FLAG™ vector (International Biotechnologies Inc., U.S.A.) is employed. Since the isolated PAP gene has a signal peptide, the coding region of mature PAP is amplified by Thermal Cycler™, which employs synthetic N-terminal and C-terminal primers. DNA thus amplified is electroeluted, digested with HindIII, and ligated into FLAG™ to form the recombinant expression vector pMJ12. Said pMJ12 was deposited with the Korean Collection of Culture and Microorganism (KCCM), an International Depository Authority (IDA) on Jun. 30, 1993 as deposition No. KCCM 10037.

pMJ12 thus constructed is transformed into competent *E. coli* HB101, and colonies transformed with pMJ12 are selected. Then, recombinant PAP is induced for 6 hrs, by culturing said colony on LB broth media containing IPTG (isopropyl-β-D-thiogalactoside) and ampicillin. After recombinant PAP induction, cells thus cultured are harvested, washed with phosphate buffered saline solution (PBS: 0.01M $NaH_2PO_4$, 0.15M NaCl, pH 7.4) two times; and lysis of the cell pellet is carried out by freezing in a dry ice-methanol bath and thawing at 37° C., repeatedly. Then, the cell lysate is centrifuged, and the supernatant thereof is collected. 10 μl of supernatant thus obtained is fractionated by SDS-PAGE, stained with Coomassie brilliant blue R, and production of recombinant PAP is determined by Western blot analysis.

For the purification of recombinant PAP, said supernatant is loaded on an anti-FLAG MI affinity column and eluted with the PBS solution containing 1.0 mM $CaCl_2$. The biological activity of recombinant PAP is determined by an in vitro translation method.

The present invention is further illustrated in the following examples, which should not be taken to limit the scope of the invention.

EXAMPLE 1

Isolation of the PAP gene from a cDNA library

PAP was isolated in accordance with Irvin's method (see: J. D. Irvin, et al., *Arch. Biochemistry Biophys.*, 169:522–528 (1975)). 480 μg of PAP was dissolved in PBS solution and combined with Freund's complete adjuvant at a ratio of 1:1 (v/v), and the mixture thereof was administered to a rabbit (~3 Kg of body weight) intramuscularly. After 3 weeks, antibody formation was detected in a small amount of blood collected from the rabbit, and 750 μg of PAP was combined with Freund's incomplete adjuvant at a ratio of 1:1 (v/v) for boosting. Plasma was fractionated from blood by centrifugation; and Protein-A agarose column chromatography was employed to isolate antibodies. An immunodiffusion assay and electrophoresis were employed to determine antibody formation and homogeneity of isolated anti-PAP antibody, respectively. Purified anti-PAP antibody was stored at –70° C. and employed to isolate the PAP gene from a cDNA library.

To isolate mRNA from the leaves of *Phytolacca americana*, the leaf tissue was homogenized using liquid nitrogen and, to the homogenate thus prepared was added a buffer solution for total RNA isolation. Centrifugation was carried out to give a supernatant; and total cellular RNA was isolated from the supernatant by LiCl sedimentation. Then, mRNA was isolated from the total RNA using oligo(dT) cellulose column chromatography, and the isolated mRNA was employed for cDNA synthesis.

First-strand cDNA was synthesized from template mRNA employing M-MuLV reverse transcriptase; and, second-strand cDNA synthesis by *E. coli* DNA polymerase followed. Synthesized cDNA was linked to an EcoRI adaptor and subjected to chromatography on Sephacryl S-400 to fractionate DNA fragments in accordance with the molecular size of the cDNA. Fractionated cDNA was ligated into the Uni-Zap XR vector (Stratagene Co., U.K.), and in vitro packaging using a packaging extract followed.

Immunoscreening employing anti-PAP antibody was carried out to isolate the PAP gene from the cDNA library thus prepared. *E. coli* SURE was infected with phage to form plaques ($2\times10^4$ pfu). Said bacteria were incubated at 37° C. for 15 min, and further cultured at 42° C. for 3.5 hours after plating with 3 ml of top agarose. Then, the plate was covered with Hybond-N+(Amersham) and incubated for 5 hours. After incubation, the Hybond-N+ was blocked with bovine serum albumin and treated with 5 mg/ml of anti-PAP antibody. After the removal of unbound anti-PAP antibody, peroxidase-conjugated secondary antibody was reacted with the anti-PAP antibody; and, antigen-antibody complexes thus formed were detected by chloronaphthol treatment.

A secondary immunoscreening procedure was performed with 15 clones obtained from the primary immunoscreening, in a similar fashion as above with the exception that $5\times10^3$ pfu were screened. A tertiary immunoscreening procedure was performed with the clones obtained from the secondary immunoscreening, and 8 positive plaques Isolated by the tertiary screen were subjected to the following experiment.

To transfer phagemids of 8 recombinant Uni-Zap XR phages, an in vivo excision technique employing R408 helper phage was carried out. Phagemids were isolated from 4 colonies by an alkali denaturation method (see: Maniatis et al., *Molecular Cloning: A Laboratory Manual*, pp 368–369, Cold Spring Harbor Laboratory (1982)), and colonies harboring the PAP cDNA insert were screened by a restriction enzyme excision method.

Of the clones thus screened, plasmids from 2 clones were isolated, and the PAP cDNA inserts were sequenced by the dideoxy chain termination method. To determine the full nucleotide sequence of the PAP gene, DNA was purified from microorganisms harboring the PAP gene. DNA thus purified was digested with SacII and BamHI, and deletions were made by an intermittent ExoIII excision reaction using the Erase-a-Base system (Promega, U.S.A.). The deleted DNAs were ligated to each other by $T_4$ DNA ligase, and the resultant plasmids were transformed into competent XL1-BLUE cell prepared by $CaCl_2$ treatment. Deletion mutants fractionated by molecular size were employed to determine the DNA sequence.

After preparation of single-stranded DNA by the alkali denaturation method, the full DNA sequence of the PAP gene was determined by SEQUENASE VERSION 2.0 (United States Biochemical, U.S.A.) employing a primer such as the $T_7$ promoter primer or the universal reverse primer. As described in FIG. 1, PAP cDNA comprises 1195 bp containing a single open reading frame (SEQ. ID. NO. 1). The cDNA insert of PAP encodes 313 amino acid residues, 22 residues of which function as a signal peptide.

EXAMPLE 2

Preparation of expression vector pMJ12

For the expression of the PAP gene in *E. coli* HB101, the commercially available FLAG™ vector (International Biotechnologies Inc., U.S.A.) was employed. Primers such as 5'-CCAAGCTTGTGAATACAATCAAC-3' SEQ. ID. No. 2 and 5'-GGAAGCTTTGATCAGAATCCTTCAAA-3' SEQ. ID. NO. 3) synthesized by a DNA Synthesizer (Applied Biosystems Inc., U.S.A.) were employed as the N-terminal primer and C-terminal primer, respectively; and the mature PAP gene was amplified by polymerase chain reaction using Vent™ DNA polymerase (New England Biolab., U.S.A.). In this connection, denaturation (95° C., 30 sec), annealing (55° C., 30 sec) and extension (72° C., 30 sec) were carried out for 30 cycles by a DNA Thermal Cycler (Cetus/Perkin-Elmer, U.S.A.). The PAP gene thus amplified was cleaved with HindIII, and the expression vector of the invention was constructed by ligating the HindIII-cleaved PAP gene with HindIII-cleaved FLAG™ vector with the aid of $T_4$ DNA ligase. The expression vector thus constructed was named pMJ12 and claimed in the invention.

The process for stepwise construction of pMJ12 is depicted in FIG. 2. In FIG. 2, S, E, X and K are employed to mean SacI, EcoRI, XhoI and KpnI restriction enzymes, respectively; and, (▇) indicates the signal peptide. pMJ12 thus constructed was transformed into competent *E. coli* HB101 prepared by CaCl treatment; and, transformants harboring pMJ12 were selected on LB media containing 50 ug/ml ampicillin, based on the plasmid DNA isolation technique employing alkaline lysis. *E. coli* HB101 thus transformed was claimed in the invention and deposited with the Korean Culture Center of Microorganisms (KCCM), an International Depository Authority (IDA) on Jun. 30, 1993, as deposition No. KCCM 10037.

FIG. 3 is a photograph showing a 0.8% agarose gel electrophoresis pattern of pMJ12 digested with HindIII. In FIG. 3, M is a molecular marker lane, i.e., λDNA fragments digested with HindIII, and the pMJ12 lane shows the expression vector pMJ12 of the present invention.

EXAMPLE 3

Growth inhibition of microorganism transformed with pMJ12

Figure 4:
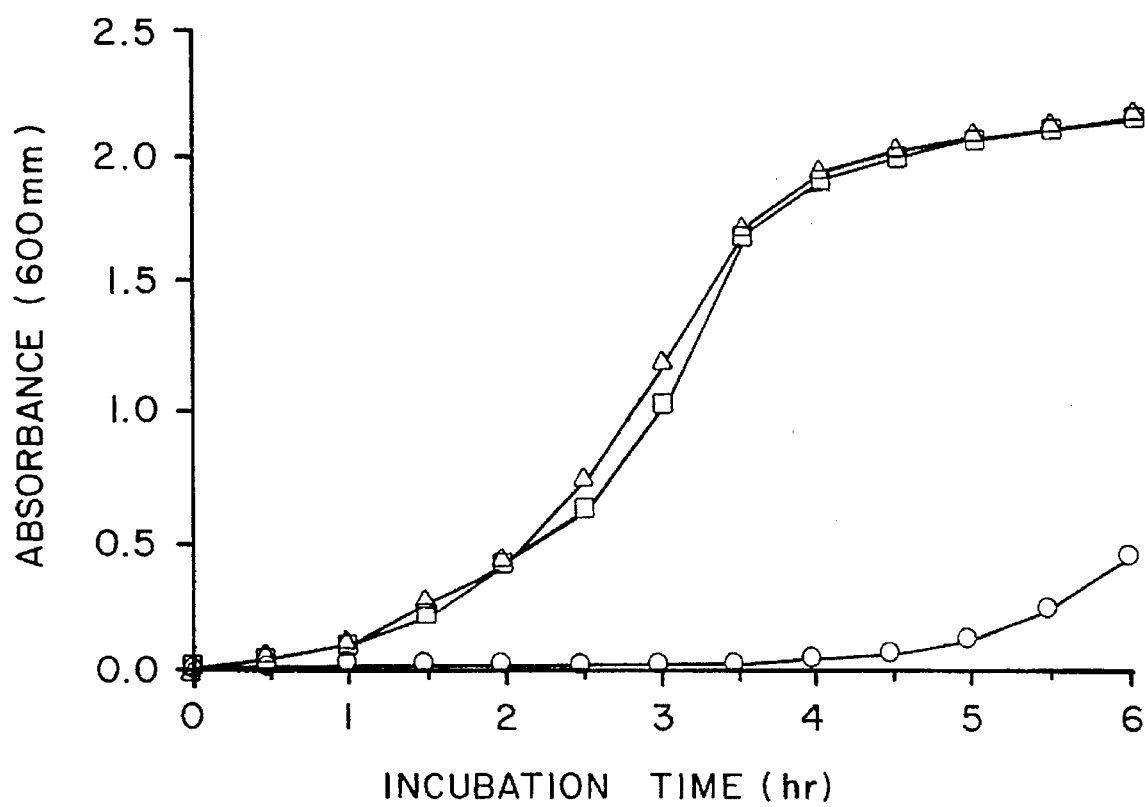
FIG. 4 is a graph showing the growth pattern of *E. coli* HB101 harboring pMJ12.

Ricin, a ribosome inactivating protein (RIP), has been reported to have no effect on the growth of host microorganisms, while expression of the MAP gene inhibits the growth of its transformant. Whether recombinant PAP produced from the expression vector pMJ12 inhibits growth of the transformant or not was studied through investigation of the cell growth pattern of the host organism. Non-transformed *E. coli* HB101 and *E. coli* HBIOI transformed with pFLAG or pMJ12 were inoculated on LB liquid media containing 50 ug/ml ampicillin, and incubated overnight. Then, each culture of the same cell concentration was pipetted, inoculated on LB liquid media containing 0.7 mM IPTG (isopropyl-β-D-thiogalactoside) and cultured on a shaking incubator at 37° C., 200 rpm; and, the cell concentration of each culture was determined by measuring absorbance at 600 nm. As clearly illustrated in FIG. 4, the growth of HB101 (O—O) harboring pMJ12 which produces recombinant PAP was inhibited remarkably, while the growth of non-transformed HB101 (△—△) and HB101 (□—□) transformed with pFLAG were normal. Accordingly, it was determined that recombinant PAP inhibits the growth of *E. coli* HB101 transformed with pMJ12 by virtue of PAP's RNA N-glycosidase activity.

EXAMPLE 4

Expression of recombinant PAP from *E. coli* HB101 transformed with vector pMJ12

*E. coli* HB101 (KCCM 10037) was cultured on 50 ml of LB medium containing 50 μg/ml ampicillin; and recombinant PAP was induced by the addition of IPTG (0.75 mM) when the $OD_{600}$ of the culture reached 1.0. After PAP induction for 6 hrs, cells thus cultured were harvested by centrifugation, washed 2 times with phosphate buffered saline (PBS: 0.01M $NaH_2PO_4$, 0.15M NaCl, pH 7.4); and subjected to freezing in dry ice-methanol bath and thawing at 37° C. Then, the cell lysate was emulsified with said buffer solution (pH 8.4) containing 0.25 mg/ml lysozyme; and the freeze/thawing process was repeated 3 times. Said solution was shaken at 10 min intervals, kept at 37° C. for 30 min, and centrifuged at 25,000×g for 45 min at 4° C. 10 μl of supernatant thus obtained was analyzed by 15% SDS-PAGE, stained with Coomassie brilliant blue R, and destained with desraining solution; and production of recombinant PAP was determined by Western blot analysis in accordance with Example 6.

EXAMPLE 5

Isolation of recombinant PAP from *E. coli* HB101 transformed with vector pMJ12

Recombinant PAP produced from *E. coli* HB101 (KCCM 10037) was isolated at 4° C., in accordance with the following procedures: To the total protein fractionated in Example 4 was added 1M $CaCl_2$ solution to a final concentration of 1.0 mM; and said solution was loaded on an anti-FLAG MI affinity gel column, after washing the column with 5 ml glycine-HCl (pH 3.0) and PBS solution 3 times. Then, said column was washed with 12 ml PBS/Ca solution (PBS solution containing 1.0 mM $CaCl_2$ solution) 3 times. 500 μl of PBS/EDTA solution (PBS solution containing 2.0 mM EDTA) was kept for 30 min in the column to which recombinant PAP was bound; the PAP was then eluted with 500 μl PBS/EDTA solution at an interval of 10 min. The amount and purity of recombinant PAP thus isolated were determined by Bradford's method (See: Bradford, *Anal Biochemistry*, 72:248 (1976); *Anal Biochemistry*, 86:142 (1978)) and SDS-PAGE analysis, respectively. The expression level of said recombinant PAP was determined to be 40 mg per 1 L of culture, which is relatively high expression compared with other RIPS. FIG. 5 is a photograph showing the SDS-PAGE pattern of purified recombinant PAP. In FIG. 5, M shows the lane containing low-molecular size markers (Pharmacia, U.S.A.); recombinant PAP is shown in the right hand lane.

EXAMPLE 6

Determination of recombinant PAP from *E. coli* HB101 transformed with vector pMJ12

Figure 6:
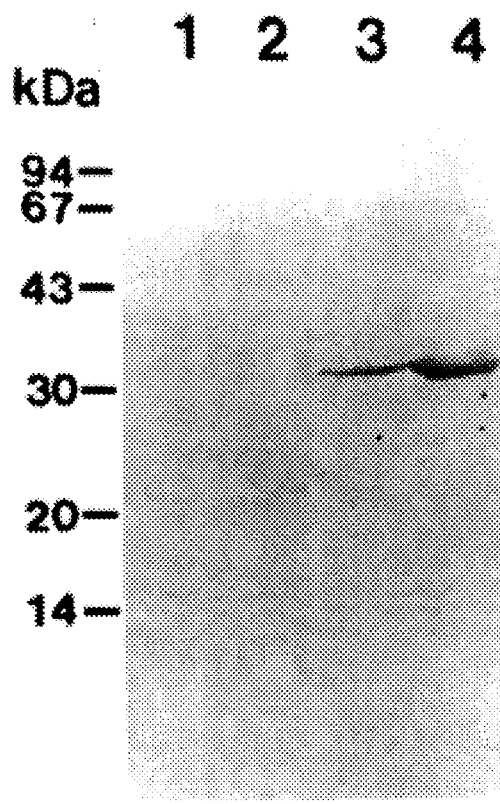
FIG. 6 is a photograph showing the Western blot analysis of PAP purified from *E. coli* HB101 harboring pMJ12; and, FIG. 7 is a photograph showing the SDS-PAGE pattern of in vitro translation employing a rabbit reticulocyte lysate system.

Total proteins of non-transformed *E. coli* HB101 and *E. coli* HB101 transformed with vector PFLAG or pMJ12 were isolated in accordance with Example 4, and Western blot analysis was performed. Protein fractionated by SDS-PAGE was transferred to Hybond-C extra (Amersham, U.K.); and, blocking was performed with a PBS solution containing 0.1% Tween 20 and 2% BSA. Said protein was washed with PBS solution (containing 0.1% Tween 20) 2 times for 5 min each; and, treated with 2 μg/ml of anti-PAP antibody at room temperature for 1 hr. Then, the filter was washed with said buffer solution 2 times, treated with rabbit peroxidase-conjugated second antibody at room temperature for 1 hr, and stained with 4-chloro-1-naphthol. As shown in the Western blot analysis of FIG. 6, only one band was detected in *E. coli* HB101 transformed with pMJ12, and no band was detected in non-transformed HB101 (lane 1) and HB101 transformed with pFLAG (lane 2).

EXAMPLE 7

Activity determination of recombinant PAP

To determine the activity of purified recombinant PAP, which inhibits protein synthesis, in vitro translation employing a rabbit reticulocyte lysate system (Promega, U.S.A.) was carried out. Recombinant PAP isolated in accordance with the Example 5 and dialyzed against deionized water using a Spectra/Por 2 membrane (Spectrum, U.S.A.), was employed for the activity determination. The reaction mixtures for in vitro translation were as disclosed in Table 1.

TABLE 1

Reaction mixtures for in vitro translation

| Experimental group | Control | PAP |
|---|---|---|
| Reaction Mixture | 35 µl rabbit reticulocyte lysate<br>1 mM amino acids (methionine free)<br>1 µl $^{35}$S-methionine (10 mCi/ml)<br>1 µl RNasin (40 U/µl)<br>2 µl luciferase RNA (0.5 µg/µl<br>11 µl Water | 35 µl rabbit reticulocyte lysate<br>1 mM amino acids (methionine free)<br>1 µl $^{35}$S-methionine (10 mCi/ml)<br>1 µl RNasin (40 U/µl)<br>2 µl luciferase RNA (0.5 µg/µl<br>11 µl recombinant PAP (80 pmol) |

Figure 7:

Each experimental group was incubated at 30° C. for 90 min. Proteins thus synthesized were fractionated by 15% SDS-PAGE, dried on a gel dryer and detected by radioautography. FIG. 7 is a photograph showing the results of SDS-PAGE after an in vitro translation experiment. As clearly illustrated in FIG. 7, protein synthesis of luciferase (62KD) is detectable in the control group (lane 1), while no protein is detected in the recombinant PAP (lane 2) group.

As clearly illustrated and demonstrated above, the present invention provides a novel expression vector for PAP and a microorganism transformed with said PAP expression vector. In accordance with the present invention, biologically active PAP can be produced in massive quantities from this microorganism. Therefore, the recombinant PAP can be applied to various fields, e.g., molecular studies on PAP and treatment of AIDS employing a PAP immunoconjugate.

What is claimed is:

1. A recombinant expression vector designated pMJ12 which directs the expression of Phytolacca antiviral protein in microorganisms.

2. *E. coli* HB101(KCCM 10037) transformed with the recombinant expression vector of claim 1, which produces Phytolacca antiviral protein.

3. A process for preparing Phytolacca antiviral protein, which comprises the steps of: (i) culturing transformed *E. coli* HB101 (KCCM 10037) cells under conditions suitable for induction of said antiviral protein; (ii) harvesting said induced cells; (iii) lysing said induced cells to produce a lysate, and centrifuging said lysate to produce a pellet and a surpernatant; and (iv) purifying said antiviral protein from said supernatant.

* * * * *